(12) United States Patent
Duan et al.

(10) Patent No.: US 9,986,898 B2
(45) Date of Patent: Jun. 5, 2018

(54) APPARATUS AND METHOD FOR CONTROLLING MOVEMENT OF A CAPSULE ENDOSCOPE IN DIGESTIVE TRACT OF A HUMAN BODY

(71) Applicants: Xiaodong Duan, Plansaton, CA (US); Shaobang Zhang, Hangzhou (CN); Guohua Xiao, Plano, TX (US); Xinhong Wang, San Diego, CA (US); Junjie Wang, Hangzhou (CN)

(72) Inventors: Xiaodong Duan, Plansaton, CA (US); Shaobang Zhang, Hangzhou (CN); Guohua Xiao, Plano, TX (US); Xinhong Wang, San Diego, CA (US); Junjie Wang, Hangzhou (CN)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 773 days.

(21) Appl. No.: 14/486,061

(22) Filed: Sep. 15, 2014

(65) Prior Publication Data
US 2015/0018614 A1    Jan. 15, 2015

Related U.S. Application Data

(63) Continuation of application No. PCT/CN2013/076162, filed on May 23, 2013.

(30) Foreign Application Priority Data

Apr. 18, 2013    (CN) .......................... 2013 1 0136094

(51) Int. Cl.
*A61B 1/00*    (2006.01)
*A61B 1/04*    (2006.01)
(Continued)

(52) U.S. Cl.
CPC ...... *A61B 1/00158* (2013.01); *A61B 1/00006* (2013.01); *A61B 1/00149* (2013.01);
(Continued)

(58) Field of Classification Search
CPC ..... A61B 1/00158; A61B 1/041; A61B 34/20; A61B 34/73; A61B 2034/731;
(Continued)

(56) References Cited

U.S. PATENT DOCUMENTS

2004/0064153 A1    4/2004    Creighton
2004/0175289 A1*   9/2004    Takizawa ............... A61B 1/041
                                                                    422/20
(Continued)

FOREIGN PATENT DOCUMENTS

CN    201012230    1/2008
CN    101732026    6/2010
(Continued)

*Primary Examiner* — Timothy J Neal
*Assistant Examiner* — Aaron B Fairchild
(74) *Attorney, Agent, or Firm* — Treasure IP Group, LLC (57) ABSTRACT

A system for controlling movement of a capsule endoscope in a human GI track is disclosed. The system comprises a magnetic dipole for placement in human GI track, an external magnet in a sphere shape generating dipole magnetic field and applying external translational and or rotational magnetic field force to the capsule endoscope, and a control system for moving the external magnet to manipulate the object along the variable axis in a desired direction of movement.

11 Claims, 6 Drawing Sheets

(51) Int. Cl.
*A61B 34/00* (2016.01)
*A61M 25/01* (2006.01)

(52) U.S. Cl.
CPC .............. *A61B 1/041* (2013.01); *A61B 34/73* (2016.02); *A61M 25/0127* (2013.01)

(58) Field of Classification Search
CPC ....... A61B 2034/732; A61B 2034/733; A61M 25/0127; A61M 25/0158
See application file for complete search history.

(56) References Cited

U.S. PATENT DOCUMENTS

2008/0300458 A1\* 12/2008 Kim .................. A61B 1/00158
600/118
2013/0303847 A1\* 11/2013 Sitti .................. A61B 1/00158
600/104

FOREIGN PATENT DOCUMENTS

| KR | 100 735 863 | 6/2007 |
|---|---|---|
| WO | 2005122866 | 12/2005 |
| WO | 2009/10789 | 9/2009 |

\* cited by examiner

Capsule gravity (g)

FIG. 9
Rotation angle of magnetic ball (Degree)

APPARATUS AND METHOD FOR CONTROLLING MOVEMENT OF A CAPSULE ENDOSCOPE IN DIGESTIVE TRACT OF A HUMAN BODY

CROSS REFERENCE TO RELATED APPLICATIONS

This application is a continuation of PCT application PCT/CN2013/076162 filed on May 23, 2013. The PCT application is incorporated herein by reference.

TECHNICAL FIELD

The invention relates to medical apparatus and instruments, specifically refers to a system and method to control movement of a capsule endoscope in a human GI track.

BACKGROUND OF THE INVENTION

Ingestible medical capsules are known in the medical arts. Such capsules telemetrically transmit information to a receiving and recording apparatus located outside the body. The wireless capsule is swallowed and travels through the digestive tract, collecting and transmitting data during the course of its journey. Receiving and recording apparatus is stationed external to the body. It is known in the art to use wireless medical capsules for collecting images by equipping them with cameras, or for delivering doses of medication to general areas of the digestive system by equipping them with drug reservoirs.

One type of currently available wireless capsules used in the medical field are carried by peristalsis through the digestive tract, and the capsule location during the journey is either unknown or only approximately known. To overcome this technology barrier, some have used wireless capsule having a permanent magnetic dipole and external magnetic field to control the position and orientation of the capsule. The external magnetic field can be generated either by a coil or a permanent magnet.

It is the goal of the present invention to provide a system and method to place a magnetic capsule endoscope in its precise location having a desired orientation.

In the same field of endeavor, most of the prior arts are silent about the importance of the shape or geometry of an external magnet and their impact on the capsule endoscope system. In the only two patent documents that were found having a geometry description in the drawings, the figures of CN 201010528466 and CN 200910273088.3, the elements providing external magnetic fields are drawn using rectangles.

Additionally, it is generally believed by anybody skilled in the art that external magnet can be of any shape/geometry and any weight. It is generally understood that the external magnet is preferred not to be in a round or globe or a ball shape, because circular contour is difficult to be manufactured, compared to other shapes, for example, square or rectangle shaped.

In the present invention, it is disclosed that contrary to the common notion in the art, the external magnetic providing the magnetic field to move and rotate a magnetic capsule endoscope, is better to be a globe shaped, in a shape of the sphere, in order to provide the best stable magnetic field. The sphere shaped magnetic provides most constant and strongest magnetic field among different shaped magnets, which is especially useful when the magnetic in the capsule endoscope is hard to be stabilized.

SUMMARY OF THE INVENTION

The present invention discloses a system for controlling movement of a capsule endoscope in human GI track comprises a magnetic dipole for placement in human GI track; an external magnet in a sphere shape generating dipole magnetic field and applying external translational and or rotational magnetic field force to the capsule endoscope; and and a control mechanism for moving the external magnet to manipulate the object along the variable axis in a desired direction of movement.

The control mechanism further comprises a base (11), wherein the system comprises a base (11), two X-axis sliding rails (12) fixed on the base (11) in parallel, at least one Y-axis sliding rail (10), vertically positioned to the X-axis sliding rails (12) along a horizontal plane, two X-axis modules (9), respectively fixed to the ends of Y-axis sliding rail (10) and slidingly joined with the X-axis sliding rails (12), a Z-axis supporting frame (7) vertically set on and slidingly-joined with the Y-axis sliding rail (10), a Z-axis sliding rail (4) vertically disposed with respect to the horizontal plane, fixed on the Z-axis supporting frame (7), a Z-axis cantilever (5) which is parallel to the horizontal plane and whose one end is slidingly-joined with the Z-axis sliding rail (4), having one end slidingly connected to Z-axis supporting frame (7) through 6.1 an enclosure frame (20) connected with the other end of the Z-axis cantilever (5), a Z-axis motor (6) driving the Z-axis cantilever (5) sliding on the Z-axis sliding rail (4), and a magnetic ball (1) installed in the frame (20), wherein the frame (20) is provided with a horizontal motor (3) controlling rotation of the magnetic ball (1) on horizontal direction, and a vertical motor (2) controlling rotation of the magnetic ball (1) on vertical direction.

DETAILED DESCRIPTION OF THE PREFERRED EMBODIMENTS

One object of the present invention is to place a capsule endoscope in a precise location in a target area, which maybe a disease area, and collect real-time medical related information so that the medical doctors can easily perform diagnose or operation on that precise target location. There are various ways have disclosed in the prior arts to navigate a capsule endoscope to a desired target area.

The present invention is mostly concerned to provide a capsule with stability once it is placed in the target area so that the doctors have enough time to collect information or perform a procedure. In one embodiment, the capsule endoscope is preferred to be stable as long as the medical procedure requires. Stable, herein, refers to a status of the capsule, which can maintain its position and orientation without a change, or a detectable change, or a noticeable change can be ignored in the desired applicable experimental or clinical settings.

The present invention discloses a system for controlling movement of a capsule endoscope in human GI track comprises
a magnetic dipole for placement in human GI track; an external magnet in a sphere shape generating dipole magnetic field and applying external translational and or rotational magnetic field force to the capsule endoscope; and
a control mechanism for moving the external magnet to manipulate the object along the variable axis in a desired direction of movement.
External Magnetic Field in a Shape of a Globe:

The shape as a globe gives the maximum volume of the magnet fitting in a three-dimensional rotating space. Thus a magnet in a shape of a globe can apply the strongest magnetic force for a magnetic capsule at the longer distance, than a magnet in any other shapes. The stronger the magnetic field the magnetic capsule can sense, the capsule can be more precisely placed into a desired location and with a desired orientation.

When the external magnet is in a shape of globe, the external magnetic field distribution is most likely to be a dipole magnetic field, having only one north pole and one south pole. When the magnetic field distribution of an external magnet in any other shapes, the magnetic field sensed by the capsule endoscope may become quadrupole or octupole. Because the dipole magnetic field is the most constant magnetic field, whereas quadrupole or octupole magnetic fields applies forces strictly dependent on where the object in located in the magnetic field. In another words, the endoscope capsule may sense different magnetic field from a multipole magnet due to mere change in its orientation, which is not desired if we want the capsule to be in a stable status for a certain period of time.

In one embodiment of the present invention, the capsule is floating in a liquid in vivo environment. The orientation and position of the capsule is more sensitive to the external magnetic field change. In order to improve the stability of the magnetic capsule in the floating environment, the external magnet is made in a shape of a globe.

In another embodiment of the present invention, the capsule is in suspension involving a liquid environment, wherein stabilizing a capsule is more difficult than capsule is anchored on the walls of a GI track. In this embodiment, it is more particular importance to provide a strong yet stable external magnetic field. Therefore the external magnetic field in a sphere shape is preferred.

The present invention is directed to a control mechanism or system for moving the external magnet to manipulate the object along the variable axis in a desired direction of movement in a human GI track. Said system comprises a base (11), two X-axis sliding rails (12) fixed on the base (11) in parallel, at least one Y-axis sliding rail (10) along a horizontal plane, vertically positioned to the X-axis sliding rails (12), two X-axis modules (9), respectively fixed to the ends of Y-axis sliding rail (10) and slidingly joined with the X-axis sliding rails (12), a Z-axis supporting frame (7) vertically set on and slidingly-joined with the Y-axis sliding rail (10), a Z-axis sliding rail (4) vertically disposed with respect to the horizontal plane, fixed on the Z-axis supporting frame (7), a Z-axis cantilever (5) which is parallel to the horizontal plane and whose one end is slidingly-joined with the Z-axis sliding rail (4), having one end slidingly connected to Z-axis supporting frame (7) through 6.1 an enclosure frame (20) connected with the other end of the Z-axis cantilever (5), a Z-axis motor (6) driving the Z-axis cantilever (5) to slide on the Z-axis sliding rail (4), and a magnetic ball (1) disposed in the enclosure frame (20), wherein the frame (20) is provided with a horizontal motor (3) controlling rotation of the magnetic ball (1) on the horizontal direction, and a vertical motor (2) controlling rotation of the magnetic ball (1) in the vertical direction.

In the above capsulate endoscope control system, said base is further provided with an X-axis motor driving the X-axis module on the X-axis sliding rail. The bottom of said Y-axis sliding rail is provided with a Y-axis base, fixed with the Y-axis sliding rail. Preferably, two of the Y-axis sliding rails are provided. By doing so, X-axis module, driven by X-axis motor, slides along X-axis sliding rail, making Y-axis sliding rail which is connected with X-axis module to slide therewith, which in turn makes the Z-axis supporting frame also slide along the Y-axis sliding rail, thereby, the magnetic ball can move along the direction parallel to X-axis sliding rail. Additionally, two Y-axis sliding rails are connected with each other through a Y-axis base, providing a more and steady movement.

In the above capsulate endoscope control system, the system further comprises a Y-axis module which is composed of side plates fixed on both sides of the Z-axis supporting frame and a baseplate fixed on the bottom thereof. Said side plate is positioned in parallel to the X-axis module, and said baseplate is in sliding contact with the Y-axis sliding rail, wherein one of the X-axis modules is provided with a Y-axis motor which drives the Y-axis module to slide on the Y-axis sliding rail, and the output end of said Y-axis motor is connected with a drive screw rod, which progressively goes through the two side plates and is connected with the screws of the two side plates. In this way, the Y-axis module, driven by the Y-axis motor, slides on the Y-axis sliding rail, making the Z-axis supporting frame, connected with Y-axis module, slide therewith, thereby the magnetic ball slide in the direction parallel to Y-axis sliding rail.

In the above capsulate endoscope control system, two of the Z-axis sliding rails and two of the Z-axis cantilevers are provided and each pair is positioned in parallel to each other. Each Z-axis cantilever has one end fixed with a Z-axis module. The two Z-axis modules are respectively slidingly joined with a Z-axis sliding rail. The Z-axis motor is positioned on the Z-axis supporting frame, and the output end of the Z-axis motor is connected with a screw rod, which is connected with two Z-axis modules through a transverse connecting rod.

Alternatively, four Z-axis sliding rails are provided and set in parallel, and two Z-axis cantilevers are provided and set in parallel. One end of each Z-axis cantilever is fixed with a Z-axis module, whose both ends are respectively slidingly joined with two Z-axis sliding rails. The two Z-axis modules are parallel to the X-axis module. The Z-axis motor is set on the Z-axis supporting frame, and the output end of Z-axis motor is connected with a screw rod, which is connected to two Z-axis modules through a transverse connecting rod.

In this way, the Z-axis module, driven by the Z-axis motor, slides on the Z-axis sliding rail, making the Z-axis supporting frame connected with Z-axis module slide therewith, thereby to control the magnetic ball to slide along the direction parallel to the Z-axis sliding rail.

In the above capsulate endoscope control system, a horizontal motor is connected with the frame via a vertical shaft. In this way, the horizontal motor controls the frame together with the magnetic ball to rotate horizontally through a vertical shaft.

In the above capsulate endoscope control system, inside the frame is provided a horizontal shaft, which passes through the magnetic ball along with a horizontal axis, and a synchronizing wheel is further installed in the supporting frame of the magnetic ball. One end of the synchronizing wheel is connected with a vertical motor, and the other end is connected with a horizontal shaft. In this way, the vertical motor drives the magnetic ball to rotate vertically through the synchronizing wheel.

In the above capsulate endoscope control system, said magnetic ball is a permanent magnet, or electromagnet, or superconducting magnet. The movement of the capsule endoscope is controlled by a small magnet, which moves in responds to the magnetic field generated by the magnetic ball.

The present invention further provides a method for controlling movement of a capsule endoscope in a human GI track, wherein said method is carried out in the following steps:

A) emptying a GI track of a subject;
B) letting the subject lie flat after taking a magnetic capsule endoscope;
C) setting up an external system to control movement of the capsule endoscope in the subject's GI track, wherein said system comprises a base, a X-axis sliding rail fixed on the base, a Y-axis sliding rail vertically positioned to the X-axis sliding rail, and two X-axis modules respectively fixed with both ends of the Y-axis sliding rail and joined with the X-axis sliding rail in a sliding way, and a Z-axis supporting frame vertically disposed on the Y-axis sliding rail and slidingly joined with the same. Wherein at least two Z-axis sliding rails vertically fixed with the Z-axis supporting frame, a Z-axis cantilever which is parallel to the horizontal plane and whose one end is joined with the Z-axis sliding rail in a sliding manner. The system further comprises a supporting frame, connected with the other end of the Z-axis cantilever; the Z-axis cantilever, driven by a Z-axis motor, to slide on a Z-axis sliding rail; and a magnetic ball placed inside the supporting frame. The supporting frame is provided with a horizontal motor to control the rotation of the magnetic ball in the horizontal direction, and a vertical motor to control the rotation in vertical direction. Said magnetic ball can be moved along the X, Y and Z axis directions, and achieve horizontal rotation and vertical spinning, thereby the distance between the magnetic ball and capsule endoscope can be adjusted to enable the capsule endoscope to be at a suspended state in a human GI track;

D) When the capsule endoscope is at a suspended state, moving the magnetic ball along the directions in parallel to X-axis sliding rail and/or Y-axis sliding rail, to make the capsule endoscope move along with the moving direction of said magnetic ball;

E) When the capsule endoscope is at a suspended state, moving the magnetic ball along the direction parallel to the Z-axis sliding rail to move the capsule endoscope opposite to the moving direction of said magnetic ball; and F) removing the capsule endoscope with human waste after the capsule endoscope has navigated through the human GI track.

In step (C) of the present invention, movements along X axis, Y axis, Z axis, horizontal rotation and vertical spinning do not interfere with each other. Each movement can either be performed alone in different time periods successively, or working at the same time, including any combination of movements.

Beneficial effects of this invention are the following. The suspension and position and posture control of a magnetic capsule endoscope in a human GI track is realized by an external magnetic field of a magnetic ball in the present invention, and, a stable suspension of the magnetic capsule endoscope is established through the magnetic field. The capsule endoscope can move in three directions along with X, Y and Z axes, and can be deflected to form various observation angles. The magnetic ball can generate the dipole type magnetic field distribution, and the magnet robot system can generate five degrees of freedom of the movement for the dipole magnetic fields. The dipole magnetic fields generates remote magnetic force to move the magnetic capsule endoscope. A method using such a magnetic ball can not only scan the surface of stomach efficiently, but also make positioning and controlling a capsule endoscope in a dynamic magnetic field become possible. Wide adoption of such a system and method can improve the detection rate of diagnosing human GI track diseases. The present invention discloses a system and method, which do not reply on the peristalsis of the human digestive track to move the capsules along. Further, the method allows for more accurate positioning and fast control, with high safety and reliability.

Figure 1:
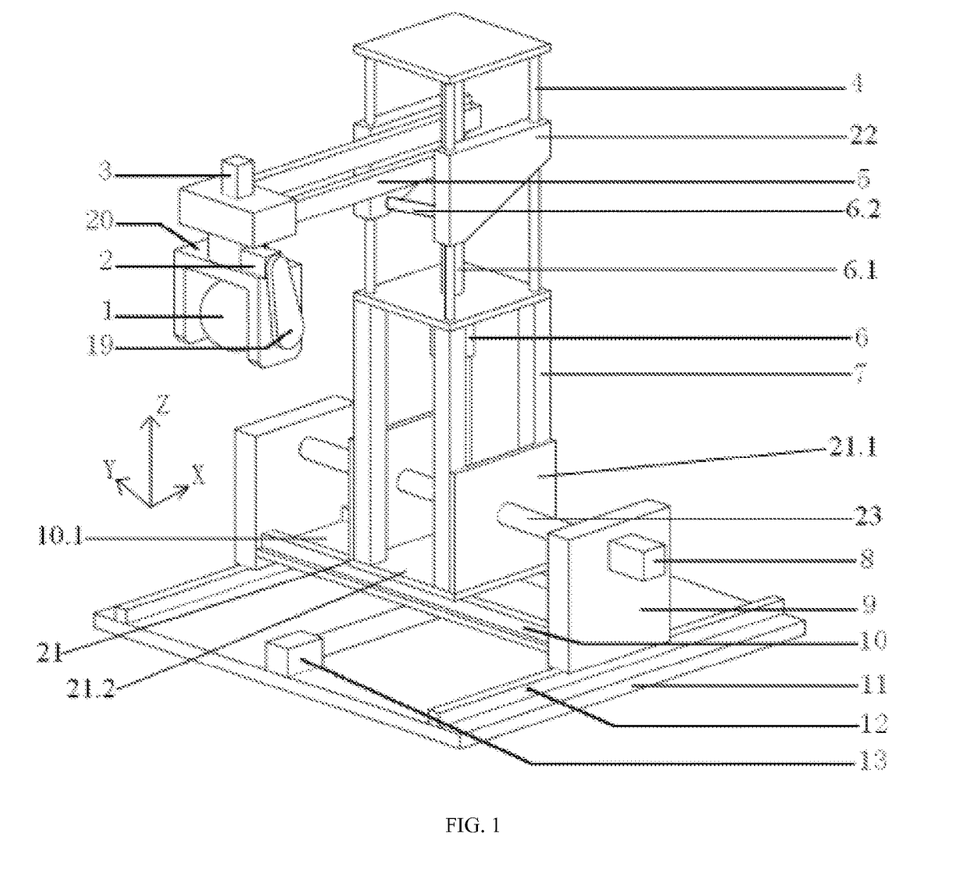
FIG. 1 is a perspective view of a system for controlling movement of capsule endoscope in human GI track.

A system for controlling the horizontal and vertical rotations of a capsule endoscope shown in FIG. 1. The system comprises a base 11, two X-axis sliding rails 12 fixed on the base 11 in parallel, two Y-axis sliding rails 10 vertically positioned to the X-axis sliding rail 12 along a horizontal plane, two X-axis modules 9 respectively fixed to the two ends of the Y-axis sliding rail 10 and slidingly-joined with the X-axis sliding rail 12. The base 11 is further provided with an X-axis motor 13, which drives the X-axis module 9 to slide on the X-axis sliding rail 12. The bottom of the Y-axis sliding rail 10 is provided with a Y-axis base 10.1, and is fixed with the same. A Z-axis supporting frame 7 is vertically set and slidingly-joined with the Y-axis sliding rail 10, and the Z-axis supporting frame 7 is provided with a Y-axis module 21. The Y-axis module 21 is comprised of side plates 21.1, fixed on both sides of the Z-axis supporting frame 7, and a baseplate 21.2, fixed on the bottom thereof. Said side plate 21.1 is parallel to the X-axis module 9, and said baseplate 21.2 is in sliding contact with the Y-axis sliding rail 10. Wherein said one of X-axis module 9 is provided with a Y-axis motor 8 which drives the Y-axis module 21 to slide on the Y-axis sliding rail 10. The output end of said Y-axis motor 8 is connected with a drive screw rod 23 successively going through the two side plates 21.1 and is screwly joined thereof.

Four paralleled Z-axis sliding rails 4 are vertically fixed on the Z-axis supporting frame 7. Two Z-axis cantilevers 5 are provided on the Z-axis supporting frame 7 and are parallel to the X-axis sliding rail 12 along a horizontal direction. One end of each Z-axis cantilever 5 is fixed with a Z-axis module 22, and the other end is connected with an enclosure frame 20. Two ends of Z-axis module 22 are respectively joined with two Z-axis sliding rails 4 in a sliding way. Two Z-axis modules 22 are parallel to the X-axis module 9. The Z-axis motor 6 is set on the Z-axis supporting frame 7. An output end of the Z-axis motor 6 is connected with a screw rod 6.1, which is further connected with two Z-axis modules 22 through a transverse connecting rod 6.2. The Z-axis module 22 slides on the Z-axis sliding rail (4) by the Z-axis motor (6), thus to move the Z-axis cantilever (5) up and down.

Figure 2:
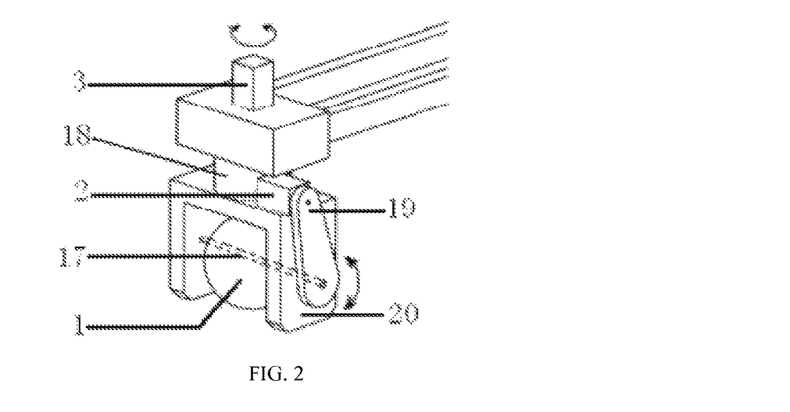
FIG. 2 is a partially perspective view of capsule endoscope in FIG. 1 for controlling horizontal and vertical rotations.

As show in FIG. 2, a magnetic ball 1 is placed in the enclosure frame 20. Said magnetic ball 1 is a permanent magnet, or electromagnet, or superconducting magnet. The enclosure frame 20 is provided with a horizontal motor 3 controlling the rotation of magnetic ball 1 on the horizontal direction, and a vertical motor 2 controlling the rotation of magnetic ball 1 on the vertical direction. The horizontal motor 3 is connected with the enclosure frame 20 via a vertical shaft 18. Wherein inside of the enclosure frame 20 is provided a horizontal shaft 17, going through said magnetic ball 1 along the horizontal axis thereof. And a synchronizing wheel 19 is further disposed in the enclosure frame 20. One end of the synchronizing wheel 19 is connected with a vertical motor 2, and the other end thereof is connected with the horizontal shaft 17.

Figure 3:
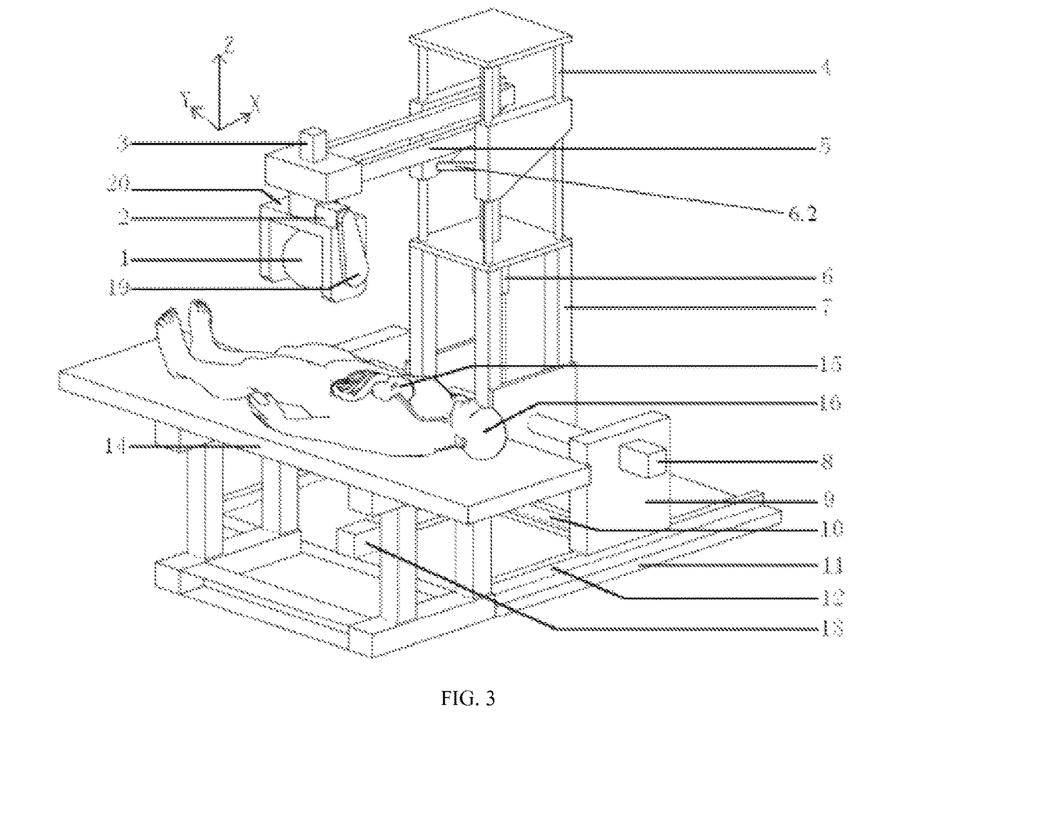
FIG. 3 is a perspective view of the system and a human, showing that the system controls movement of the capsule endoscope in a Human GI track.

As shown in FIG. 3, a method for controlling movement of a capsule endoscope in a human GI track using above system is performed in the following steps:

A) abrosia within 4 to 12 hours before the experiment, and emptying GI track as much as possible in order to prevent in vivo residues influencing the photography by the capsule endoscope;

B) letting a subject 16 lie flat on a bench 14 after taking a capsule endoscope 15 containing a magnet;

C) setting said external system for controlling the motion of a capsule endoscope 15 in a human GI track of the subject 16, and the X-axis motor 13, Y-axis motor 8, and Z-axis motor 6 are provided to respectively adjust movements of the X-axis module 9, Y-axis module 21, and Z-axis module 22, which enables the magnetic ball 1 to move along X axis, Y axis and Z axis. And the horizontal motor 3 and vertical motor 2 are respectively controlled to enable the magnetic ball 1 to rotate horizontally and vertically, thereby to control the distance between said magnetic ball 1 and magnetic capsule endoscope 15. By doing so, the magnetic capsule endoscope 15 can be suspended when the total of the floating force and the attraction force given by the magnetic ball 1, which the capsule receives, is the same as the gravity it experiences.

When the system is at work, X-axis motor 13, Y-axis motor 8, Z-axis motor 6, horizontal motor 3 and vertical motor 2 do not interfere with each other. They are not only capable of working alone in different time periods separately, but also joined-working as five motors at the same time, or working in combinations. If five motors work at the same time, X-axis module 9, Y-axis module 21, and Z-axis module 22 slide at the same time, and the enclosure frame 20 drives the magnetic ball 1 spinning on horizontal direction, at this time, said magnetic ball 1 also can rotate around the vertical shaft on vertical direction;

D) When the capsule endoscope is suspended, controlling X-axis motor 13 and/or Y-axis motor 8, the magnetic ball 1 will move along the direction parallel to the X-axis sliding rail 12 and/or Y-axis sliding rail 10, namely, the magnetic ball 1 will move along the X-axis or Y-axis. Because of the receipt of gradually increasing magnetic field force in the corresponding direction, the capsule endoscope 15 moves along in the movement direction of the magnetic ball 1;

E) When the capsule endoscope is suspended, controlling said Z-axis motor 6, the Z-axis module 22 connected with the Z-axis cantilever 5 will slide on the Z-axis sliding rail 4 up and down, then the magnetic ball 1 will also move up and down along the Z-axis, and correspondingly, the capsule endoscope 15 also moves up and down by the change of the magnetic force between magnet ball and the capsule endoscope; and F) based on above steps of said method, controlling the capsule endoscope 15 to move through a certain or whole human GI track, and then discharge the capsule endoscope with human waste.

The above embodiments are only preferable embodiments of the invention, and are not used to limit this invention. Although the invention is specified in detail referring to aforesaid embodiment, technicians of this field still can modify the technical solution recorded in each aforesaid embodiment, or replace partial technical features and the like therein. Any replacement, improvement and the like made within spirits and principles of the invention shall be included in protection scope of the invention.

Stable Suspension Experiments

The invention further implements a stable suspension experiment on the aforesaid system, verifying the feasibility of the invention for controlling the movement of a capsule endoscope in a human GI track.

Said capsule endoscope 15 of the following experiments comprises a magnet.

Figure 4:
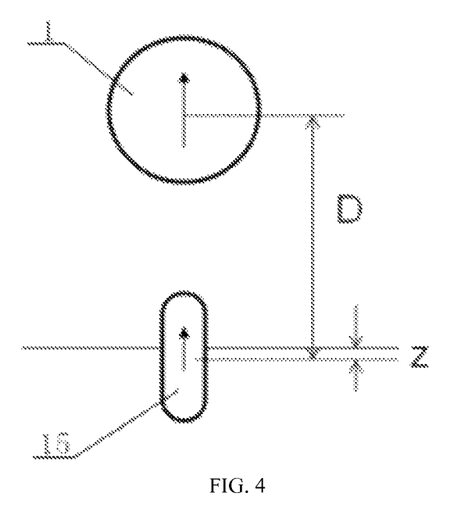
FIG. 4 is a schematic diagram for stable suspension of a capsule endoscope in the invention.
Figure 5:
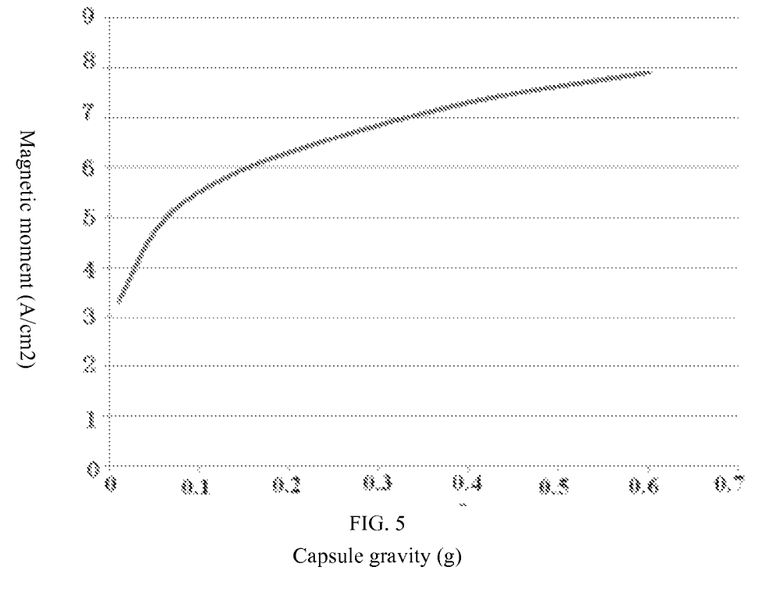
FIG. 5 depicts a maximum weight allow for a capsule to be float or suspended based on the magnetic moment of the capsule in accordance with the aspects of the present invention.

When its gravity density is more than the liquid density, capsule endoscope 15 performs stable self-suspension relying on external magnetic force, as shown in FIG. 4. The requirement of the weight and magnetic moment of capsule in order to be suspended is listed in FIG. 5, wherein the y axis is the gravity that the capsule endoscope experienced, or the weight of the capsule endoscope, and x axis is the magnetic moment of the capsule. Any capsule in the area underneath the curve depicted in FIG. 5 can be suspended.

A capsule endoscope 15 in suspension because of the magnetic force:

$$F_m + F_{float} = W$$

Wherein, W is the gravity of capsule endoscope 15, $F_m$ is the magnetic force applied to the capsule endoscope 15, $F_{float}$ is floating force on capsule endoscope 15.

$$F_m = \frac{\mu_0}{4\pi} \frac{6Mm}{(D+z)^4}$$

$$F_{float} = \rho_{liquid}(L/2 + z)\pi R^2$$

Wherein, M is the magnetic moment of the magnetic ball 1 under action of magnetic force; m is magnetic moment of the magnet in the capsule endoscope 15 under the magnetic field force; as shown in FIG. 4, D is the distance from magnetic ball 1 to capsule endoscope 15, z is the distance between gas-liquid interface of a human GI track and center of the capsule endoscope 15, L is the length of capsule endoscope 15, R is radius of capsule endoscope 15, $\rho_{liquid}$ is a liquid density in the Human GI track, $\mu_0$ is the permeability of vacuum.

In order to achieve stable suspension of a magnetic capsule, following conditions shall be satisfied:

$$\frac{\partial(W - F_m - F_{float})}{\partial r} = \frac{\mu_0}{\pi} \frac{6Mm}{(D - L/2)^5} - \rho_{liquid}\pi R^2 < 0$$

$$D/L > 4\rho_{capsule}/\rho_{liquid} + \frac{1}{2}$$

Wherein $\rho_{liquid}$ is a liquid density in Human GI track, $\rho_{capsule}$ is a density of capsule endoscope 15.

Figure 6:
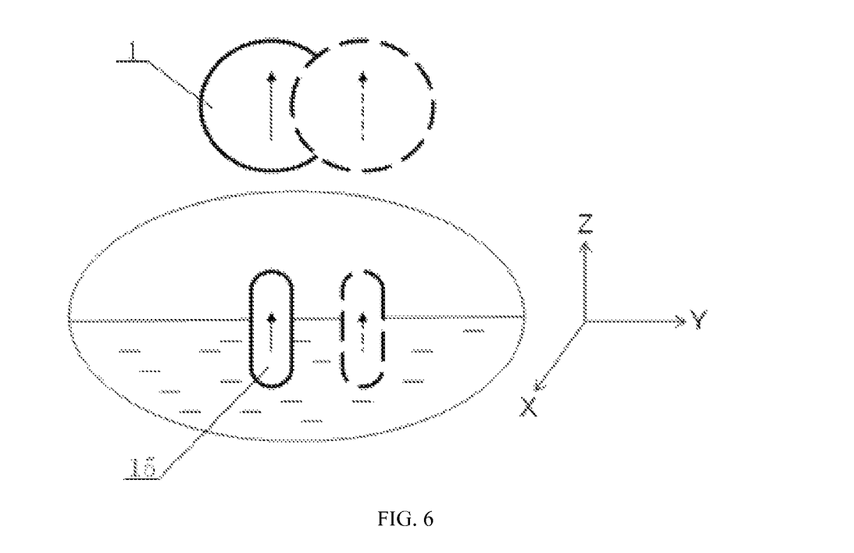
FIG. 6 is a schematic diagram of a capsule endoscope moving on X axis while floating.
Figure 7:
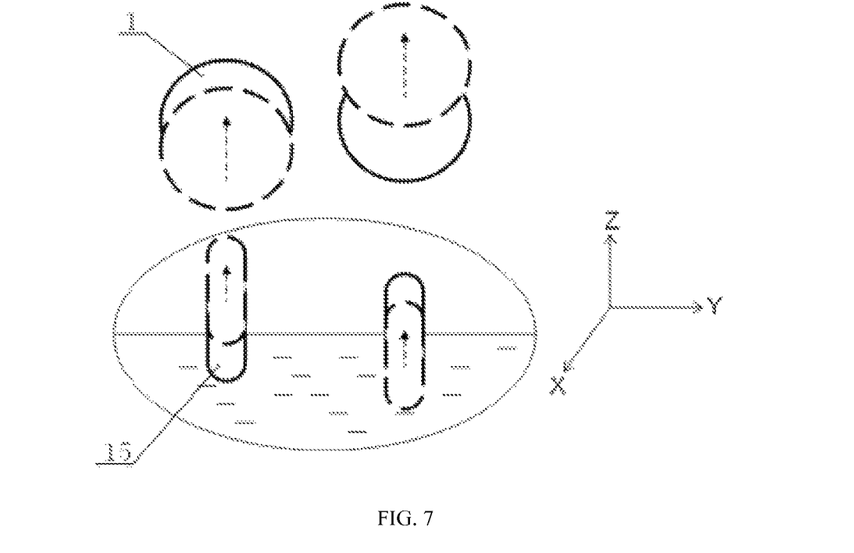
FIG. 7 is a schematic diagram of a capsule endoscope moving on Z axis while floating.

Precise movements of the capsule endoscope 15 on X, Y, and Z axis are controlled by the magnetic ball 1, as shown in FIG. 6 and FIG. 7.

Under a condition of suspension, as shown in FIG. 6, when the magnetic ball 1 is moved on X and Y axis, the capsule endoscope 15 in vivo also moves on X and Y axis horizontally.

Under a condition of suspension, as shown in FIG. 7, when the magnetic ball 1 is moved along the Z axis, and when the magnetic ball 1 moves downwards, the capsule endoscope 15 in vivo moves upwards; and when magnetic ball 1 moves upwards, the capsule endoscope 15 in vivo moves downwards. Movements of the capsule endoscope 15 in vivo on Z axis can be precisely controlled via controlling the movement of the magnetic ball 1 in the Z axis direction. In this way, the top or bottom of gastric mucosa can be observed either remotely or closely.

Suspension and rotation methods of capsule endoscope 15 on a particular point are as shown in FIGS. 8 to 11, a capsule endoscope 15 is placed in a angular manner on a particular point of the gas-liquid interface in a human GI track. The magnetic ball 1 moves in opposite direction to adjust the capsule endoscope 15 to a desired location in the Z axis direction. In this way, the capsule endoscope 15 can adjust its own angles in any given point. This is a method to use capsule endoscope 15 in suspension to inspect a stomach surface.

Figure 8:
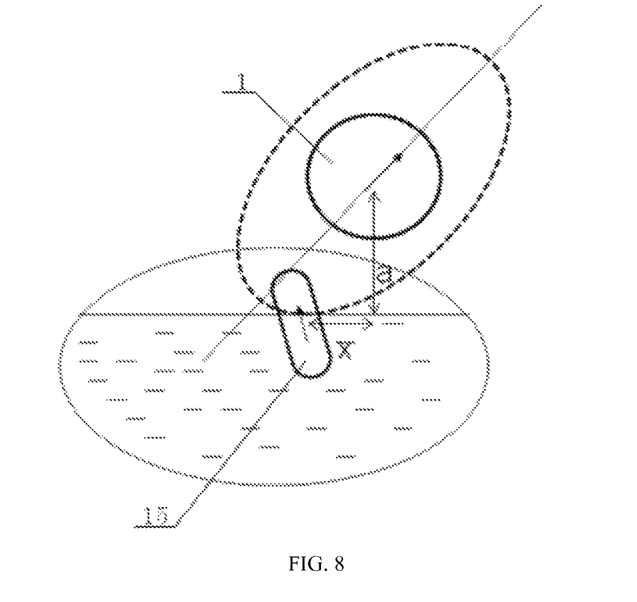
FIG. 8 is a schematic diagram of a capsule endoscope rotating in the external magnetic field while floating.

Under a condition of suspension, as shown in FIG. 8, when magnetic ball 1 rotates towards a same direction, capsule endoscope in vivo also rotates therewith. However, if the maximum magnetic-field location changes, the capsule endoscope in vivo posses a horizontal offset distance from the original location thereof. The dashed ellipse in FIG. 8 is the magnetic equipotential line, the point of contact of the dashed ellipse with gas-liquid interface in human GI track is the maximum point of magnetic field intensity, and the changing curve of the horizontal distance deviating from the original location and the rotation angle of the magnetic ball 1 is as shown in FIG. 9.

Figure 10:
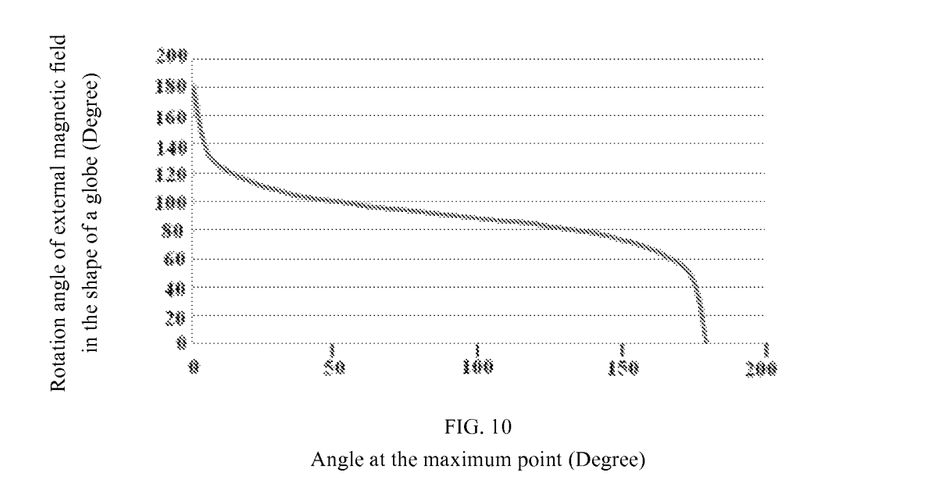
FIG. 10 is the relationship between the angle of the maximum magnetic field point and rotation angle for the magnetic ball.

FIG. 10 shows a changing curve of angle in the maximum magnetic field intensity point and rotation angle for the magnetic ball. Rotation angles of the magnetic ball 1 are changed to control the tilt angles of capsule endoscope 15. Additionally, FIG. 10 further shows that the tilt angles of the capsule endoscope 15 within 45 degrees to 135 degrees are more easily to be controlled than others.

Figure 9:
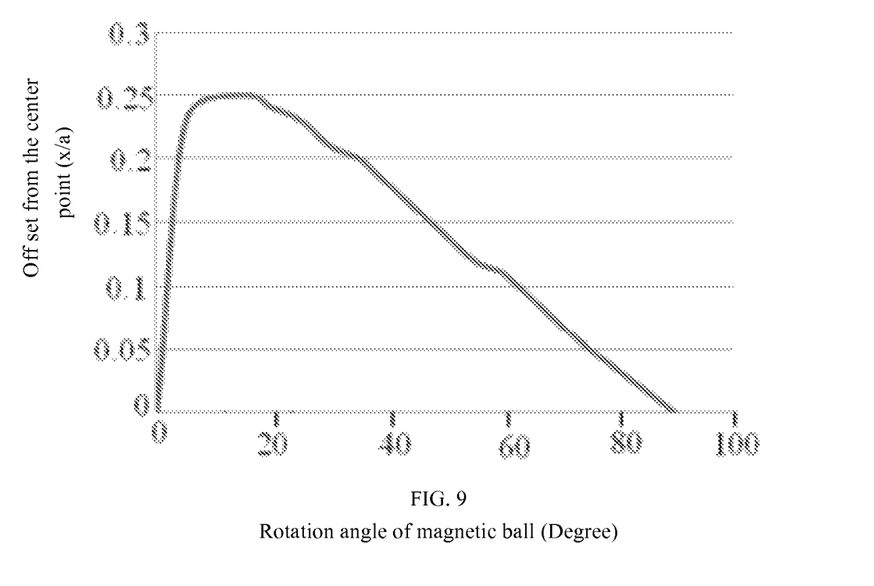
FIG. 9 is the relationship between the horizontal movement of the capsule endoscope in response to the rotation angle of the external magnetic ball while the capsule is floating.
Figure 11:
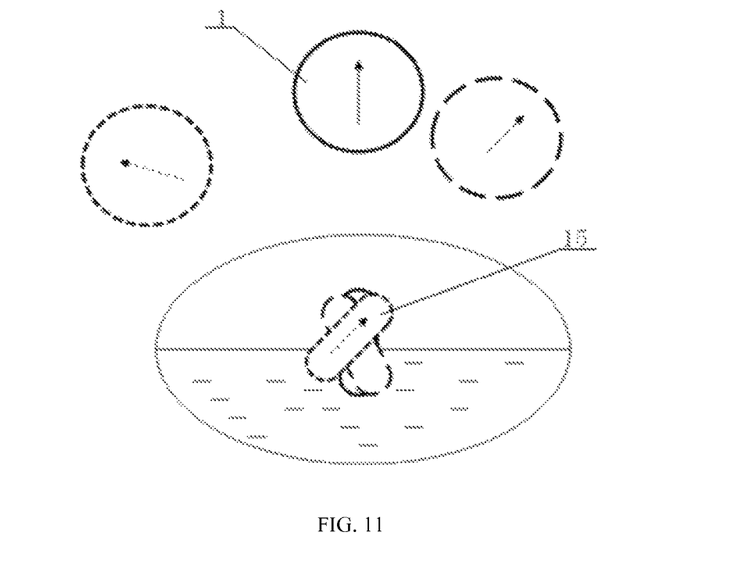
FIG. 11 is a stepwise illustration of the angle change of capsule endoscope in response to the movement of the external magnetic field.

As shown in FIG. 11, when angles of capsule endoscope 15 are changed, the magnetic ball 1 self-rotates and moves along the section of XYZ axis to compensate the distance of moving as shown in FIG. 9, therefore, the capsule endoscope 15 moves and rotates nearby, and in this way, it is beneficial for observing specific conditions around mucosa of a GI track.

The invention claimed is:

1. A capsulate endoscope control system, comprising
a base (11),
two X-axis sliding rails (12), fixed on the base (11) in parallel,
at least one Y-axis sliding rail (10), vertically positioned to the X-axis sliding rails (12) along a horizontal plane,
two X-axis modules (9), respectively fixed to ends of the at least one Y-axis sliding rail (10) and slidingly joined with the X-axis sliding rails (12),
a Z-axis supporting frame (7) vertically set on and slidingly-joined with the at least one Y-axis sliding rail (10),
a Z-axis sliding rail (4) vertically disposed with respect to the horizontal plane, fixed on the Z-axis supporting frame (7),
a Z-axis cantilever (5) which is parallel to the horizontal plane and whose one end is slidingly-joined with the Z-axis sliding rail (4), the Z-axis cantilever (5) having one end slidingly connected to the Z-axis supporting frame (7) through a screw rod (6.1), and the other end of the Z-axis cantilever (5) connected with a frame (20),
a Z-axis motor (6) driving the Z-axis cantilever (5) sliding on the Z-axis sliding rail (4), and
a magnetic ball (1) installed in the frame (20),
wherein the frame (20) is provided with a horizontal motor (3) controlling rotation of the magnetic ball (1) in a horizontal direction, and a vertical motor (2) controlling rotation of the magnetic ball (1) in a vertical direction.

2. The system of claim 1, wherein the base (11) is further provided with
an X-axis motor (13), which is configured to drive the X-axis module (9) to slide on the X-axis sliding rail (12), and a bottom of the at least one Y-axis sliding rail (10) is provided with a Y-axis base (10.1) fixedly therewith.

3. The system of claim 1, wherein
the at least one Y-axis sliding rails are two Y-axis sliding rails (10).

4. The system of claim 1, further comprises
a Y-axis module (21) which is comprised of side plates (21.1), fixed on both sides of the Z-axis supporting frame (7), and
a baseplate (21.2) fixed on a bottom thereof, said side plate (21.1) being parallel to the X-axis module (9), and said baseplate (21.2) being in sliding contact with the at least one Y-axis sliding rail (10),
wherein
one of said X-axis modules (9) is provided with a Y-axis motor (8) which drives the Y-axis module (21) to slide on the at least one Y-axis sliding rail (10), and
an output end of said Y-axis motor (8) is connected with a drive screw rod (23) successively pass through the side plates (21.1) and a screw jointed thereof.

5. The system of claim 1, wherein
said horizontal motor (3) is connected with the frame (20) via a vertical shaft (18).

6. The system of claim 1, wherein
a horizontal shaft (17) is provided inside the frame (20) and across through the magnetic ball (1), along a horizontal axis thereof, and a synchronizing wheel (19) is disposed in the frame (20), one end of the synchronizing wheel (19) being connected with a vertical motor (2), and the other end thereof being connected with the horizontal shaft (17).

7. The system of claim 1, wherein the system is configured to change orientation of a capsule endoscope while the capsule endoscope is suspended at a gas/liquid interface.

8. The system of claim 1, wherein the magnetic ball is configured to be horizontally rotated relative to the frame.

9. The system of claim 1, wherein the magnetic ball is configured to be spun vertically relative to the frame.

10. The system of claim 1, wherein the magnetic ball is configured to adjust a tilt angel of a capsule endoscope when the tilt angle relative to a gas/liquid interface is between 45-135 degrees.

11. A method of using the system of claim 1, comprising:
controlling the magnetic ball (1) to move along a direction parallel to the X-axis slide rail (12) and/or the at least one Y-axis slide rail (10), enabling a capsule endoscope (15) to move along a moving direction of the magnetic ball (1); and
controlling the magnetic ball (1) to move along a direction parallel to the Z-axis slide rail (14), enabling the capsule endoscope (15) to move opposite to another moving direction of the magnetic ball (1), wherein the capsule endoscope is suspended at a gas/liquid interface.

* * * * *